United States Patent [19]
Dowbenko et al.

[11] Patent Number: 4,749,803
[45] Date of Patent: Jun. 7, 1988

[54] REACTION PRODUCTS OF MERCAPTO-FUNCTIONAL MONOHYDRIC ALCOHOLS AND VINYL SILANES, AND NCO-FUNCTIONAL COMPOUNDS THEREFROM

[75] Inventors: Rostyslaw Dowbenko, Gibsonia; Debra L. Singer, Pittsburgh, both of Pa.

[73] Assignee: PPG Industries, Inc., Pittsburgh, Pa.

[21] Appl. No.: 816,078

[22] Filed: Jan. 3, 1986

[51] Int. Cl.$^4$ .......................... C07F 7/10; C07F 7/18
[52] U.S. Cl. ..................................... 556/414; 556/427
[58] Field of Search ................................ 556/414, 427

[56] References Cited

U.S. PATENT DOCUMENTS 3,404,168 10/1968 Simmler et al. ................ 556/427 X
3,502,704  3/1970 McKellar ........................ 556/427 X
3,691,222  9/1972 Wendel ............................. 556/427

OTHER PUBLICATIONS

"The Chemistry of Acrylovitrile", 2nd ed., American Cyananid Co., N.Y. (1959), p. 26.

*Primary Examiner*—Paul F. Shaver
*Attorney, Agent, or Firm*—Thomas M. Breininger

[57] ABSTRACT

Disclosed is an adduct of a mercapto-functional monohydric alcohol and a vinyl-type silane having at least one hydrolyzable group directly attached to a silicon atom, the adduct prepared by reacting the mercapto-functional monohydric alcohol and the vinyl-type silane in the presence of a free radical initiator.

Also disclosed is an NCO-functional compound comprising the reaction product of: (A) the aforesaid adduct of a mercapto-functional monohydric alcohol and a vinyl-type silane having at least one hydrolyzable group directly attached to a silicon atom, and (B) an organic polyisocyanate.

12 Claims, No Drawings

REACTION PRODUCTS OF MERCAPTO-FUNCTIONAL MONOHYDRIC ALCOHOLS AND VINYL SILANES, AND NCO-FUNCTIONAL COMPOUNDS THEREFROM

BACKGROUND OF THE INVENTION

Certain isocyanato-functional compounds which also contain silicon atoms bonded to hydrolyzable groups such as gamma-isocyanatopropyl triethoxy silane are known in the art.

The present invention is directed to a new class of isocyanato-functional compounds which contain thio groups and also contain silicon atoms bonded to hydrolyzable groups.

The present invention is also directed to a new class of compounds which are useful for preparing the isocyanato-functional compounds which contain thio groups and also contain silicon atoms bonded to hydrolyzable groups.

SUMMARY OF THE PRESENT INVENTION

The present invention is for an adduct of a mercapto-functional monohydric alcohol and a vinyl-type silane having at least one hydrolyzable group directly attached to a silicon atom, the adduct prepared by reacting the mercapto-functional monohydric alcohol and the vinyl-type silane in the presence of a free radical initiator.

The present invention is also for an NCO-functional compound comprising the reaction product of: (A) the aforesaid adduct of a mercapto-functional monohydric alcohol and a vinyl-type silane having at least one hydrolyzable group directly attached to a silicon atom, and (B) an organic polyisocyanate.

DETAILED DESCRIPTION OF THE INVENTION

An adduct of the present invention corresponds to the following formula (I)

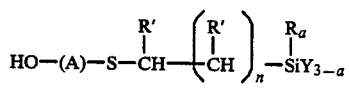

(I)

wherein
A is the residue of a mercapto-functional monohydric alcohol, each Y, which may be the same or different, represents a hydrolyzable group,
each R, which may be the same or different, represents a $C_1-C_4$ alkyl group, a vinyl group or an allyl group, preferably a $C_1-C_4$ alkyl group, and more preferably methyl,
each R', which may be the same or different, represents H or a $C_1-C_4$ alkyl group, preferably H,
a represents an integer of from 0 to 2, preferably an integer of from 0 to 1, and most preferably 0, and
n represents an integer of from 1 to 2, preferably 1.

Examples of groups suitable as the hydrolyzable group Y include: $-OR^1$,

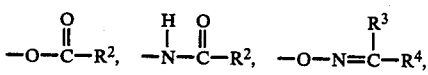

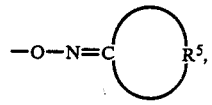

and the monohydroxy and/or cyclic $C_2-C_3$ residue of a 1,2- or 1,3-glycol, wherein
$R^1$ represents $C_1-C_4$ alkyl,
$R^2$ independently represents H or $C_1-C_4$ alkyl,
$R^3$ and $R^4$ independently represent H, $C_1-C_4$ alkyl, $C_6-C_8$ aryl and
$R^5$ represents $C_4-C_7$ alkylene.

Preferred hydrolyzable groups include $C_1-C_4$ alkoxy groups, and more preferred hydrolyzable groups include methoxy groups.

Illustrative of vinyl-type silanes, having at least one hydrolyzable group directly attached to a silicon atom, which may be utilized to provide the structure

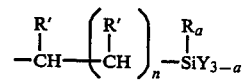

in formula (I) above include: vinylalkoxysilanes such as vinyltrimethoxysilane, methylvinyltrimethoxysilane, vinyltriethoxysilane, methylvinyltriethoxysilane, vinylmethyldimethoxysilane, vinylethyldiethoxysilane, and vinyltris(2-methoxyethoxy)silane; vinylacetoxysilanes, such as vinylmethyldiacetoxysilane, vinylethyldiacetoxysilane and vinyltriacetoxysilane; allylalkoxysilanes such as allyltrimethoxysilane, allylmethyldimethoxysilane, and allyltriethoxysilane; divinylalkoxysilanes and divinylacetoxysilanes such as divinyldimethoxysilane, divinyldiethoxysilane and divinyldiacetoxysilane; diallylalkoxysilanes and diallylacetoxysilanes such as diallyldimethoxysilane, diallyldiethoxysilane and diallyldiacetoxysilane; as well as other similar ethylenically unsaturated silane monomers containing one or more hydrolyzable groups. As will be appreciated by one skilled in the art given the present disclosure, use of compounds such as divinyl-group-containing silanes (e.g., divinyldimethoxysilane) and diallyl-group-containing silanes (e.g., diallyldimethoxysilane) can provide structures

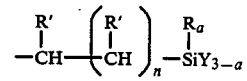

in formula (I) above in which, for example, the group R can be a vinyl group (e.g., $-CH=CH_2$) or an allyl group (e.g., $-CH_2-CH=CH_2$). In such an instance, the Si atom will be bonded to either one or two hydrolyzable groups. It is also possible that more complex structures can be formed, for example, by reaction of both vinyl-type groups on, for example, a divinyl-group-containing silane monomer with mercapto groups on different mercapto-functional monohydric alcohols.

Of the vinyl-type silane monomers described above, the monovinyl-type silane monomers (e.g., vinyltrimethoxysilane or vinylmethyldimethoxysilane as contrasted with divinyl-type silane monomers) are preferred. More preferred vinyl-type silane monomers include vinyl alkoxy silanes especially those having 1 to 4 carbon atoms in the alkoxy group. Particularly preferred vinyl alkoxy silanes are vinyl trialkoxy silanes selected from the group consisting of vinyl trimethoxy silane, vinyl triethoxy silane and a mixture thereof.

It is to be understood that mixtures of vinyl-type silanes having at least one hydrolyzable group directly attached to a silicon atom may be utilized.

The adduct is typically prepared by reacting the vinyl-type silane monomer such as those described above with a mercapto-functional monohydric alcohol in the presence of a free radical initiator. However, where desired, free radicals may be generated by the action of ultraviolet light or ionizing particle radiation such as electron beam radiation, on compounds containing, for example, suitable ethylenic unsaturation which can generate free radicals upon application of ultraviolet light or ionizing radiation. Typically, however, a free radical initiator is utilized in the preparation of an adduct of the invention. Examples of suitable free radical initiators include: azo compounds such as, for example, alpha alpha'-azobis(isobutyronitrile) and 2,2'-azobis(2,4-dimethylvaleronitrile) (available as VAZO 67); peroxides such as benzoyl peroxide and cumene hydroperoxide; and tertiary butyl peracetate, isopropyl percarbonate, butyl isopropyl peroxy carbonate and similar compounds. The amount of free radical initiator used generally ranges from 0.1 mole to 1 mole of initiator per mole of mercapto functionality or vinyl-type unsaturation.

Illustrative of suitable mercapto-functional monohydric alcohols suitable for providing the group HO-(A)- as found in formula (I) above are: 2-mercaptoethanol, 1-mercapto-3-propanol, 3-mercapto-2-butanol, and the like. It is to be understood that mixtures of mercapto-functional monohydric alcohols may be utilized.

Generally the addition reaction of the vinyl silane monomer with the mercapto-functional monohydric alcohol is carried out in an organic solvent medium. Organic solvents which may be utilized include, virtually any of the organic solvents heretofore employed for vinyl addition reactions such as involved in the solution polymerization of more conventional vinyl-type monomers such as acrylic monomers. Examples of such organic solvents include alcohols, ketones, aromatic hydrocarbons or mixtures thereof. Illustrative of organic solvents of the above type which may be employed are alcohols such as lower alkanols containing 2 to 4 carbon atoms including ethanol, propanol, isopropanol, and butanol; ether alcohols such as ethylene glycol monoethyl ether, ethylene glycol monobutyl ether, propylene glycol monomethyl ether, and dipropylene glycol monoethyl ether; ketones such as methyl ethyl ketone, methyl N-butyl ketone, and methyl isobutyl ketone; esters such as butyl acetate; and aromatic hydrocarbons such as xylene, toluene, and naphtha.

The free radical addition reaction of the vinyl silanes having at least one hydrolyzable group directly attached to a silicon atom with the mercapto-functional monohydric alcohol is generally carried out in a temperature range of from about 80 to about 120 degrees Celsius, preferably from about 85 to about 95 degrees Celsius depending on the initiator used.

It is believed that the high yield of adduct corresponding to formula (I) which results is attributable at least in part to the fact that the vinyl-type silane monomer, such as the vinyl alkoxy silane monomer, does not tend to homopolymerize in the preparation of the adduct of the invention. Rather it adds essentially 1 to 1 with the HS- group of the mercapto-functional monohydric alcohol in the presence of the free radical initiator.

An NCO-functional compound of the invention can be prepared by reacting (A) the aforesaid adduct of a mercapto-functional monohydric alcohol and a vinyl-type silane having at least one hydrolyzable group directly attached to a silicon atom, with a stoichiometric excess of (B) an organic polyisocyanate.

The organic polyisocyanate may be aromatic, aliphatic, cycloaliphatic, or heterocyclic and may be unsubstituted or substituted with groups such as halogen, etc. Many such organic polyisocyanates are known, examples of which include: toluene-2,4-diisocyanate, toluene-2,6-diisocyanate, and mixtures thereof; diphenylmethane-4,4'-diisocyanate, diphenylmethane-2,4'-diisocyanate and mixtures thereof; para-phenylene diisocyanate; biphenyl diisocyanate; 3,3'-dimethyl-4,4'-diphenylene diisocyanate; tetramethylene-1,4-diisocyanate; hexamethylene-1,6-diisocyanate; 2,2,4-trimethyl-hexane-1,6-diisocyanate; lysine methyl ester diisocyanate; bis(isocyanatoethyl)fumarate; isophorone diisocyanate; ethylene diisocyanate; dodecane-1,12-diisocyanate; cyclobutane-1,3-diisocyanate; cyclohexane-1,3-diisocyanate, cyclohexane-1,4-diisocyanate and mixtures thereof; methylcyclohexyl diisocyanate; hexahydrotoluene-2,4-diisocyanate, hexahydrotoluene-2,6-diisocyanate and mixtures thereof; hexahydrophenylene-1,3-diisocyanate, hexahydrophenylene-1,4-diisocyanate and mixtures thereof; perhydrodiphenylmethane-2,4'-diisocyanate, perhydrodiphenylmethane-4,4'-diisocyanate and mixtures thereof. It is to be understood that mixtures of polyisocyanates and monoisocyanates may be utilized as the organic polyisocyanate. Moreover, isocyanate prepolymers may be utilized as the polyisocyanate. Isocyanate prepolymers refer to the reaction products of a polyol and polyisocyanate in which the polyol and polyisocyanate are reacted, by the generally known prepolymer technique, in relative proportions to produce an isocyanato-functional product, namely the isocyanate prepolymer. Also, mixtures of organic isocyanate prepolymers with monomeric isocyanates (so-called semi-prepolymers) may be utilized in the prepolymer technique.

Examples of polyols useful in the preparation of the isocyanate prepolymers include: organic polyols in the broad classes including: (a) simple diols, triols, and higher hydric alcohols; (b) polyester polyols; (c) polyether polyols; (d) amide-containing polyols; (e) acrylic polyols; (f) epoxy polyols; (g) polyhydric polyvinyl alcohols; and (h) urethane polyols.

(a) The simple diols, triols, and higher hydric alcohols are generally known, examples of which include: ethylene glycol; propylene glycol; 1,2-butanediol; 1,4-butanediol; 1,3-butanediol; 2,2,4-trimethyl-1,3-pentanediol; 1,5-pentanediol; 2,4-pentanediol; 1,6-hexanediol; 2,5-hexanediol; 2-methyl-1,3-pentanediol; 2-methyl-2,4-pentanediol; 2,4-heptanediol; 2-ethyl-1,3-hexanediol; 2,2-dimethyl-1,3-propanediol; 1,4-cyclohexanediol; 1,4-cyclohexanedimethanol; 1,2-bis(hydroxymethyl)cyclohexane; 1,2-bis(hydroxyethyl)cyclohexane; 2,2-dimethyl-3-hydroxypropyl-2,2-dimethyl-3-hydroxypropionate; diethylene glycol; dipropylene glycol; bis hydroxypropyl hydantoins; tris hydroxyethyl isocyanurate; the alkoxylation product of 1 mole of 2,2-bis(4-hydroxyphenyl)propane (i.e., bisphenol-A) and 2 moles of propylene oxide available as DOW-565 from DOW Chemical Company; and the like.

(b) Polyester polyols are generally known and are prepared by conventional techniques utilizing simple diols, triols and higher hydric alcohols known in the art including but not limited to the previously described simple diols, triols, and higher hydric alcohols (optionally in combination with monohydric alcohols) with polycarboxylic acids. Examples of suitable polycarboxylic acids include: phthalic acid; isophthalic acid; terephthalic acid; trimellitic acid; tetrahydrophthalic acid, hexahydrophthalic acid; tetrachlorophthalic acid; adipic acid, azelaic acid, sebacic acid; succinic acid; malic acid; glutaric acid; malonic acid; pimelic acid; suberic acid; 2,2-dimethylsuccinic acid; 3,3-dimethylglutaric acid; 2,2-dimethylglutaric acid; maleic acid, fumaric acid, itaconic acid; and the like. Anhydrides of the above acids, where they exist, can also be employed and are encompassed by the term "polycarboxylic acid". In addition, certain materials which react in a manner similar to acids to form polyester polyols are also useful. Such materials include lactones such as caprolactone, propylolactone and methyl caprolactone, and hydroxy acids such as hydroxycaproic acid and dimethylolpropionic acid. If a triol or higher hydric alcohol is used, a monocarboxylic acid, such as acetic acid and benzoic acid, may be used in the preparation of the polyester polyol, and for some purposes, such a polyester polyol may be desirable. Moreover, polyester polyols are understood herein to include polyester polyols modified with fatty acids or glyceride oils of fatty acids (i.e., conventional alkyd polyols containing such modification). Another suitable polyester polyol is one prepared by reacting an alkylene oxide such as ethylene oxide, propylene oxide, butylglycidyl ether, and the glycidyl esters of organic acids such as CARDURA-E, with the carboxylic acid to form the corresponding ester.

Examples of the optional monohydric alcohols which may be used to prepare the polyester polyols include: ethanol, propanol, isopropanol, n-pentanol, neopentyl alcohol, 2-ethoxyethanol, 2-methoxyethanol, 1-hexanol, cyclohexanol, 2-methyl-2-hexanol, 2-ethylhexyl alcohol, 1-octanol, 2-octanol, 1-nonanol, 5-butyl-5-nonanol, isodecyl alcohol, and the like.

Alkyd polyols typically are produced by reacting polyhydric alcohols, polycarboxylic acids, and fatty acids derived from drying, semi-drying or non-drying oils in various proportions depending upon the extent of hydroxyl functionality and properties desired in the alkyd polyol. The techniques of preparing such alkyd polyols are well known generally. Usually, the process involves reacting together the polycarboxylic acid and fatty acid or partial glyceride thereof and the polyhydric alcohol (the latter usually in stoichiometric excess) in the presence of a catalyst such as litharge, sulfuric acid, or sulfonic acid to effect esterification with evolution of water. Examples of polyhydric alcohols typically used for preparation of the alkyd polyols include the simple diols, triols and higher hydric alcohols known in the art including but not limited to the previously described simple diols, triols, and higher hydric alcohols. Examples of polycarboxylic acids suitable for preparation of the alkyd polyols include those set forth previously in the description of polycarboxylic acids useful for preparing polyester polyols. Examples of suitable fatty acids include saturated and unsaturated acids such as stearic acid, oleic acid, ricinoleic acid, palmitic acid, linoleic acid, linolenic acid, licanic acid, elaeostearic acid, clupanodonic acid and mixtures thereof. The fatty acids may be in the form of the free acids with sufficient excess of the polyhydric alcohol being incorporated into the esterification mixture to compensate for their inclusion. However, in many instances, glyceride oils may be employed which have been partially alcoholized with sufficient amount of a polyhydric alcohol such as glycerol to supply the requisite amount of available hydroxyls for formation of the alkyd polyol.

(c) Polyether polyols are generally known. Examples of polyether polyols include the poly-(oxyethylene) glycols and poly-(oxypropylene) glycols prepared by the acid or base catalyzed addition of ethylene oxide or propylene oxide to initiators such as ethylene glycol, propylene glycol, diethylene glycol and dipropylene glycol and by the copolymerization of ethylene oxide and propylene oxide with initiator compounds such as trimethylolpropane, glycerol, pentaerythritol, sorbitol, sucrose and the like. Examples of polyether polyols also include the generally known poly-(oxytetramethylene) glycols prepared by the polymerization of tetrahydrofuran in the presence of Lewis acid catalysts such as boron trifluoride, tin (IV) chloride, antimony pentachloride, antimonytrichloride, phosphorous pentafluoride, and sulfonyl chloride. Other examples of polyether polyols include the generally known reaction products of 1,2-epoxide-containing compounds with polyols such as those included in the description of simple diols, triols, and higher hydric alcohols above.

(d) Amide-containing polyols are generally known and typically are prepared from any of the above-described diacids or lactones and diols, triols and higher alcohols, and diamines or aminoalcohols as illustrated, for example, by the reaction of neopentyl glycol, adipic acid and hexamethylenediamine. The amide-containing polyols also may be prepared through aminolysis by the reaction, for example, of carboxylates, carboxylic acids, or lactones with aminoalcohols. Examples of suitable diamines and aminoalcohols include hexamethylenediamine, ethylenediamine, phenylenediamines, toluenediamines, monoethanolamine, diethanolamine, N-methyl-monoethanolamine, isophorone diamine, 1,8-menthanediamine and the like.

(e) Acrylic polyols include but are not limited to the known hydroxyl-functional addition polymers and copolymers of acrylic and methacrylic acids and their ester derivatives including but not limited to their hydroxyl-functional ester derivatives, acrylamide and methacrylamide, and unsaturated nitriles such as acrylonitrile and methacrylonitrile. Additional examples of acrylic monomers which can be addition polymerized to form acrylic polyols include hydroxyethyl (meth)acrylate, hydroxypropyl (meth)acrylate, methyl (meth)acrylate, ethyl (meth)acrylate, propyl (meth)acrylate, isopropyl (meth)acrylate, butyl (meth)acrylate, t-butyl (meth)acrylate, 2-ethylhexyl (meth)acrylate, n-hexyl (meth)acrylate, cyclohexyl (meth)acrylate, 3,3,5-trimethylcyclohexyl (meth)acrylate, decyl (meth)acrylate, isodecyl (meth)acrylate, lauryl (meth)acrylate, stearyl (meth)acrylate, phenyl (meth)acrylate, and isobornyl (meth)acrylate.

(f) Epoxy polyols are generally known and can be prepared, for example, by the reaction of glycidyl ethers of polyphenols such as the diglycidyl ether of 2,2-bis (4-hydroxyphenyl) propane, with polyphenols such as 2,2-bis (4-hydroxyphenyl) propane. Epoxy polyols of varying molecular weights and average hydroxyl functionality can be prepared depending upon the ratio of starting materials used.

(g) Polyhydric polyvinyl alcohols are generally known and can be prepared, for example, by the addition polymerization of vinyl acetate in the presence of suitable initiators followed by hydrolysis of at least a portion of the acetate moieties. In the hydrolysis process, hydroxyl groups are formed which are attached directly to the polymer backbone. In addition to homopolymers, copolymers of vinyl acetate and monomers such as vinyl chloride can be prepared and hydrolyzed in similar fashion to form polyhydric polyvinyl alcohol-polyvinyl chloride copolymers.

(h) Urethane polyols are generally known and can be prepared, for example, by reaction of an organic polyisocyanate with a polyol. Examples of polyisocyanates useful in the preparation of urethane polyols include those described above as exemplary of component (B) in the discussion of a preparation of NCO-functional compounds of the invention. Examples of polyols useful in the preparation of isocyanate prepolymers include those described in subsections (a) through (g) above.

Of the polyols described above for preparation of the NCO-functional compounds of the invention utilizing isocyanate prepolymers, polyhydroxyl-functional esters and acrylic polyols are preferred, polyhydroxyl-functional esters being more preferred. The term "polyhydroxyl-functional esters" is intended to include both oligomeric ester polyols such as 2,2-dimethyl-3-hydroxypropyl-2,2-dimethyl-3-hydroxypropionate and polyester polyols described above.

The mercapto-functional monohydric alcohol and the vinyl-type silane typically are reacted, in the presence of the free radical initiator, to form the aforesaid adduct, in a separate step from reaction of the adduct with the organic polyisocyanate. Of course, it will be appreciated, given the disclosure herein, that the order of reacting the components can be varied. For example, the organic isocyanate may first be reacted with the mercapto-functional monohydric alcohol to form a product, and thereafter the aforesaid product may be reacted with the vinyl silane monomer in the presence of a suitable free radical initiator. This illustrative alternate method may be suitable when it is desired also to incorporate moieties such as -NH-CO-S- in the NCO-functional compounds of the invention.

It will be appreciated by one skilled in the art, given the disclosure herein, that the NCO-functional compounds of the invention can be further reacted with compounds containing active hydrogen atoms, examples of which include but are not limited to polyols such as, for example, those described herein previously.

NCO-functional compounds of the invention can be utilized, for example, to prepare urethane resins which contain silicon atoms bonded to hydrolyzable groups which urethane resins can be cured in the presence of atmospheric moisture via reaction of the hydrolyzable groups with moisture.

The examples which follow are submitted for the purpose of further illustrating the nature of the invention and utility of the invention and should not be construed as a limitation on the scope thereof.

As used in the body of the specification, examples, and claims, all percents, ratios and parts are by weight unless otherwise specifically indicated. Wherever used herein, "pbw" means "parts by weight".

EXAMPLE 1

This example illustrates in parts (a) and (b) respectively: the preparation of an adduct of a mercapto-functional monohydric alcohol and a vinyl silane having at least one hydrolyzable group directly attached to a silicon atom; and the preparation of an NCO-functional compound which is the reaction product of the aforesaid adduct of a mercapto-functional monohydric alcohol and a vinyl silane having at least one hydrolyzable group directly attached to a silicon atom, with an organic polyisocyanate. Part (c) illustrates the preparation of a urethane resin containing silicon atoms bonded to hydrolyzable groups utilizing an NCO-functional compound (of the invention) containing silicon atoms bonded to hydrolyzable groups. Parts (d) and (e) illustrate the preparation and curing of a coating composition utilizing the urethane resin of part (c).

(a) A reaction vessel equipped with thermometer, Dean Stark trap and means for maintaining a nitrogen blanket is charged with 564.0 g of toluene and 3200.0 g of 2-mercaptoethanol and heated to reflux under a blanket of nitrogen to a temperature of 127 degrees C. and held at reflux for 6½ hours while the pot temperature ranges between 127 and 130 degrees C. Over the aforesaid period a total of 53 g of distillate containing water is removed. The mercapto equivalent weight of the dried mercapto ethanol solution in the vessel at this point is 95.6.

Next 243 g of toluene is added to the vessel and the contents of the vessel are heated to 90 degrees C. Next the addition of three charges are begun simultaneously to the contents of the vessel. Charge I consists of 1656.0 g of the dried mercaptoethanol solution. Charge II consists of 2962.0 g of vinyl trimethoxy silane. Charge III consists of 43.7 g of 2,2'-azobis(2,4-dimethylvaleronitrile) (i.e.,VAZO 67) dissolved in 120.0 g of toluene. Charges I and II and about 3/4 of charge III are added to the contents of the vessel over a period of 1½ hours while the temperature is maintained at about 90 degrees C. When the additions of charges I and II are complete 20.0 g of toluene is added to the contents of the vessel through the addition funnel used for charge I and 20.0 g of toluene is added through the addition funnel used for charge II. The remainder of charge III is added over an additional ½ hour while the temperature is maintained at about 90 degrees C. When the addition of charge III is complete, 20.0 g of toluene is added to the contents of the vessel through the addition funnel used for charge III. Thereafter the contents of the vessel are held at 90 degrees C. for 1 hour and thereafter allowed to cool to 60 degrees C.

The product in the vessel at this point is an adduct of a mercapto-functional monohydric alcohol and a vinyl silane having at least one hydrolyzable group directly attached to a silicon atom.

(b) Next, charge IV consisting of 3996.0 g of isophorone diisocyanate is added over a period of 30 minutes to the contents of the vessel while the temperature drops to 45 degrees C. Next the contents of the vessel are heated over 20 minutes to 60 degrees C. and held at about 60 degrees C. for 1 hour. Next the contents of the vessel are heated over a period of 15 minutes to 75 degrees C. and held at 75 degrees C. for 5 hours and 15 minutes after which heating is discontinued and the contents of the vessel allowed to cool to room temperature.

The resulting product has an NCO equivalent weight of 479, a viscosity of 0.68 Stokes, a Gardner color value of 1 to 2, and a total solids content measured for 1 hour at 110 degrees C. of 73.1 percent by weight. The product is an NCO-functional compound which is the reaction product of the aforesaid adduct of a mercapto-functional monohydric alcohol and a vinyl silane having at least one hydrolyzable group directly attached to a silicon atom, and an organic polyisocyanate.

(c) A reaction vessel equipped with thermometer, stirrer, reflux condenser, and means for maintaining a nitrogen blanket is charged with 705.0 g of a polyester polyol composition described in footnote 1 below, 1739.5 g of the product of part (b) immediately above, and 476.8 g of toluene and is heated under a nitrogen blanket for ½ hour to 60 degrees C. and held for 1 hour at 60 degrees C. Next, the contents of the vessel are heated over 15 minutes to 85 degrees C. and thereafter held at 85 degrees C. for 5½ hours after which heating is discontinued and the contents of the vessel allowed to cool to ambient temperature. Next the contents of the vessel are heated over 1 hour and 15 minutes to 85 degrees C. and held for 3 hours at 85 degrees C. Thereafter, heating is discontinued and the contents of the vessel allowed to cool to about 60 degrees at which temperature 16.1 g of methanol are added to the vessel. Thereafter the contents of the vessel are allowed to cool to ambient temperature.

[1] A polyester polyol composition prepared using 164.2 pbw hexahydrophthalic anhydride, 285.8 pbw trimethylolpropane, and 10.4 pbw butyl stannoic acid catalyst, at 75 percent by weight solids in methyl amyl ketone, having an acid value of between 8 and 10 and a Gardner Holdt bubble tube viscosity of between V and Y. On resin solids the polyester polyol composition contains about 56 percent by weight trimethylol propane hexahydrophthalate and 44 percent by weight excess trimethylol propane.

The resultant product is a urethane resin and has an NCO equivalent weight of infinity; a Gardner color value of 2; a viscosity of 12.7 Stokes; a total solids content measured for 1 hour at 110 degrees C. of 69.1 percent by weight; a weight average molecular weight of 4475, a peak molecular weight of 440 and a polydispersity index of 5.08 as measured by gel permeation chromatography using a polystyrene standard.

(d) A coating composition is formulated as set forth in the following Table 1.

TABLE 1

| Composition | |
|---|---|
| | Amount in grams |
| Methyl ethyl ketone | 51.4 |
| Dibutyl tin dilaurate | 3.0 |
| Resultant product resin of Example 5(b) | 142.9 |
| Total Weight | 197.3 |
| No. 4 Ford Cup Viscosity in seconds | 17.2 |
| Theoretical Percent Total Solids | 52.2% |

(e) Two samples of the Composition as described in Table 1 of the resulting clear films is cured for 30 minutes at 285 degrees F. (141 degree C.) and the other is cured at ambient temperature in air for 3 days.

Each of the cured films is tested for Sward Hardness and solvent resistanace[1]. The results are as set forth in the following Table 2.

TABLE 2

| Sward Hardness | |
|---|---|
| 30 min./285° F. | 94 |
| Ambient Cure | 66 |
| Solvent Resistance | |
| 30 min/285° F. | good |
| Ambient Cure | good |

[1] Solvent resistance is tested by rubbing each of the films using 20 back-and-forth finger rubs with a cloth dipped in xylene and observing for deterioration of the film as evidenced by marring due to softening when rubbed.

The test results of this example would indicate that a composition containing, as the sole film former, a urethane resin prepared from an NCO-functional compound of the invention such as the one described in this example could be utilized to provide hard, solvent resistant films.

What is claimed is:

1. An NCO-functional compound comprising the reaction product of:
   (A) an adduct of a mercapto-functional monohydric alcohol and a vinyl-type silane having at least one hydrolyzable group directly attached to a silicon atom, said adduct prepared by reacting said mercapto-functional monohydric alcohol and said vinyl-type silane in the presence of a free radical initiator; and
   (B) an organic diisocyanate.

2. The NCO-functional compound of claim 1 wherein said hydrolyzable group, each of which may be the same or different, is selected from the group consisting of $-OR^1$,

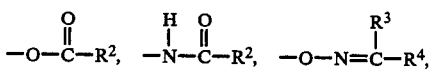

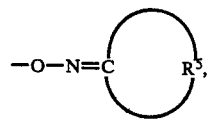

and the monohydroxy and/or cyclic $C_2$–$C_3$ residue of a 1,2- or 1,3-glycol, wherein
$R^1$ represents $C_1$–$C_4$ alkyl,
$R^2$ independently represents H or $C_1$–$C_4$ alkyl,
$R_3$ and $R_4$ independently represent H, $C_1$–$C_4$ alkyl, $C_6$–$C_8$ aryl and
$R^5$ represents $C_4$–$C_7$ alkylene.

3. The NCO-functional compound of claim 1 wherein said hydrolyzable group, each of which may be the same or different, represents a $C_1$–$C_4$ alkoxy group.

4. An NCO-functional compound comprising the reaction product of:
   (A) an adduct of a mercapto-functional monohydric alcohol and a vinyl-type silane having at least one hydrozyable group directly attached to a silicon atom, said adduct prepared by reacting said mercapto-functional monohydric alcohol and said vinyl-type silane in the presence of a free radical initiator; and
   (B) an organic diisocyanate; wherein said adduct corresponds to the formula

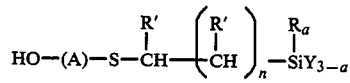

wherein
A is the residue of said mercapto-functional monohydric alcohol, each Y, which may be the same or different, represents a hydrolyzable group, each R, whcih may be the same of different, represents a $C_1$-$C_4$ alkyl group, a vinyl group or an allyl group, each R', may be the same or different, represents H or a $C_1$-$C_4$ alkyl group, a represents an integer of from 0 to 2, and n represents an integer of from 1 to 2.

5. The NCO-functional compound of claim 4 wherein a is an integer of from 0 to 1 and R is a $C_1$-$C_4$ alkyl group.

6. The NCO-functional compound of claim 5 wherein n is 1.

7. The NCO-functional compound of claim 6 wherein R' is hydrogen.

8. A process for preparing a hydroxyl-functional sulfur-containing silane having at least one hydrolyzable group comprising: reacting in the presence of a free radical initiator, a mercapto-functional monohydric alcohol with a vinyl-type silane having at least one hydrolyzable group directly attached to a silicon atom.

9. The process of claim 9 wherein said vinyl-type silane is a vinyl trialkoxy silane.

10. The process of claim 9 wherein said vinyl trialkoxy silane is selected from the group consisting of vinyl trimethoxy silane, vinyl triethoxy silane and a mixture thereof.

11. The process of claim 8 wherein said hydrolyzable group, each of which may be the same or different, is selected from the group consistin of $-OR^1$, $$-O-\overset{O}{\underset{\|}{C}}-R^2, \quad -\overset{H}{\underset{|}{N}}-\overset{O}{\underset{\|}{C}}-R^2, \quad -O-N=\overset{R^3}{\underset{|}{C}}-R^4,$$

$$-O-N=C\begin{pmatrix}\\R^5\\\end{pmatrix},$$

and the monohydroxy and/or cycllic $C_2$-$C_3$ residue of a 1,2- or 1,3-gylcol, wherein $R^1$ represents $C_1$-$C_4$ alkyl, $R^2$ independently represents H or $C_1$-$C_4$ alkyl, $R^3$ and $R^4$ independently represents H, $C_1$-$C_4$ alkyl, $C_6$-$C_8$ aryl and $R^5$ represents $C_4$-$C_7$ alkylene.

12. The process of claim 8 wherein said hydrolyzable group, each of which may be the same or different, represents a $C_1$-$C_4$ alkoxy group.

* * * * *

UNITED STATES PATENT AND TRADEMARK OFFICE
CERTIFICATE OF CORRECTION

PATENT NO. : 4,749,803

DATED : June 7, 1988

INVENTOR(S) : Rostyslaw Dowbenko et al.

It is certified that error appears in the above-identified patent and that said Letters Patent is hereby corrected as shown below:

Column 10, line 52, claim 4; "hydrozyable" should read --hydrolyzable--.

Column 11, line 1, claim 4; "whcih may be the same of different," should read --which may be the same or different,--.
          line 4, claim 4; after "R'," insert --which--.
          line 22, claim 9 should be dependent on claim 8.

Column 12, line 15, claim 11; "cycllic" should read --cyclic--.
          line 19, claim 11; "represents" should read --represent--.

Signed and Sealed this

Twenty-second Day of November, 1988

Attest:

DONALD J. QUIGG

*Attesting Officer*      *Commissioner of Patents and Trademarks*